(12) United States Patent
Williams

(10) Patent No.: US 11,583,751 B2
(45) Date of Patent: Feb. 21, 2023

(54) LOW PROFILE ARTICULATION JAW JOINT STABILIZER DEVICE

(71) Applicant: Edward D. Williams, Philadelphia, PA (US)

(72) Inventor: Edward D. Williams, Philadelphia, PA (US)

( * ) Notice: Subject to any disclaimer, the term of this patent is extended or adjusted under 35 U.S.C. 154(b) by 740 days.

(21) Appl. No.: 16/269,308

(22) Filed: Feb. 6, 2019

(65) Prior Publication Data

US 2020/0038736 A1 Feb. 6, 2020

Related U.S. Application Data

(63) Continuation of application No. 15/155,728, filed as application No. PCT/US2015/060308 on Nov. 12, 2015, now abandoned, which is a continuation-in-part of application No. 14/544,024, filed on Nov. 17, 2014, now abandoned.

(51) Int. Cl.
*A63B 71/08* (2006.01)
*A61F 5/56* (2006.01)

(52) U.S. Cl.
CPC ............ *A63B 71/085* (2013.01); *A61F 5/566* (2013.01); *A63B 2071/086* (2013.01)

(58) Field of Classification Search
CPC ... A63B 71/085; A63B 2071/086; A61F 5/56; A61F 5/566; A61M 16/049; A61M 16/0493
See application file for complete search history.

(56) References Cited

U.S. PATENT DOCUMENTS 5,636,379 A * 6/1997 Williams ............. A63B 71/085
128/862
6,935,857 B1 8/2005 Farrell
(Continued)

OTHER PUBLICATIONS

International Search Report and Written Opinion dated Feb. 24, 2016 in connection with PCT/US2015/060308 (11 pages).

*Primary Examiner* — Keri J Nelson
(74) *Attorney, Agent, or Firm* — Fox Rothschild LLP; Gary Hecht; P. Marshall Ticer

(57) ABSTRACT

The diagnosed soft tissue or brain injury component of concussions is generally defined by the symptoms of the temporal lobe manifestations. However, there is an undiagnosed structural fractured component of concussions occurring within the jaw joint complex which is the focus of this invention. A precise imaging technique and the powerful 3D Cone beam scanning technology, together, have revealed fractures in temporal bones of the jaw joint space which supports the temporal lobe of the brain. These fractures are the results of the lower jaw impact forces that cause concussions and this mechanism account for a large percent of the concussions arising in sports and military operations. These fractures have never been considered, diagnosed, or treated in the management of concussions. Fracturing temporal bones in the jaw joint that supports the temporal lobe will certainly produce the symptoms of temporal lobe manifestations. With early detection, these fractures can be more rapidly healed, eliminating many temporal lobe symptoms of concussions. The device of the present invention reduces the risk of the lower jaw impact concussion and temporal bone fractures, while enhancing the ability to speak and orally communicate.

16 Claims, 4 Drawing Sheets

SIDE VIEW

(56) References Cited

U.S. PATENT DOCUMENTS

| | | | |
|---|---|---|---|
| 6,986,354 B1 | 1/2006 | Burns | |
| 8,419,595 B1 * | 4/2013 | Hanswirth | A63B 23/032 |
| | | | 482/11 |
| 8,585,401 B2 * | 11/2013 | Moses | A63B 71/085 |
| | | | 433/37 |
| 8,689,795 B2 * | 4/2014 | Lee | A61F 5/566 |
| | | | 433/7 |
| 2010/0326433 A1 | 12/2010 | Williams | |
| 2011/0005531 A1 | 1/2011 | Manzo | |
| 2013/0029291 A1 | 1/2013 | Williams | |
| 2013/0104913 A1 | 5/2013 | Evans et al. | |
| 2013/0146066 A1 | 6/2013 | Croll | |

* cited by examiner

OCCLUSAL VIEW

FRONTAL VIEW

LINGUAL VIEW

FRONTAL VIEW

SIDE VIEW

MID-SAGITTAL VIEW

LOW PROFILE ARTICULATION JAW JOINT STABILIZER DEVICE

CROSS-REFERENCE TO RELATED APPLICATION

This application is a continuation of U.S. application Ser. No. 15/155,728, filed May 16, 2016, which is a U.S. National Phase of International Application No. PCT/US2015/060308, filed Nov. 12, 2015, which claims priority to U.S. patent application Ser. No. 14/544,024, filed Nov. 17, 2014. The contents of the foregoing applications are hereby incorporated by reference in their entireties.

FIELD OF THE INVENTION

This invention relates to a device that not only protects the teeth, oral cavity and jaw joint alignment while engaging in exercise, sports and/or other physical activities but also enhances the clarity of speech and speech communication and forming oral sounds while wearing the device. More particularly, this invention will align and stabilize the lower jaw while protecting and balancing the jaw joint complex, the teeth, and oral cavity. At the same time, it will enhance mouth breathing and the articulation of speech during physical and mental events (e.g., jaw joint rehabilitation, exercise, fitness, physical training, playing a sport, sleeping, physical therapy activities, and military operations) while wearing the low profile articulation jaw joint stabilizer device.

BACKGROUND OF THE INVENTION

In the prior art, the difficulty of clear, accurate and audible sound production while wearing mouth guards of any type made these product less desirable and problematic to wear in all sports due to the inability to speak, call signals, cadences, plays, and or expressing other critical or essential sounds for on or off-field-communications.

Athletes in all sports at all levels are becoming bigger, stronger, and faster. There are numerous studies and substantial medical evidence that various recreational activities and collision sports involving children, adolescents, young adults, professional athletes and military personnel are causing an unprecedented number of brain concussions and an unexpected finding of jaw joint (temporal mandibular joint) or basal skull fractures. This is especially so with regard to collision activities such as football, basketball, boxing, soccer, hockey, lacrosse, military operations and the like. The Center for Disease Control and Prevention (CDC) reported that each year, as many as 3.8 million sports and recreation-related concussions occur in the United States. All concussions involve some level of brain injury. The highest rates occur among males aged 10-19. While the soft tissue injury components of concussions (the brain) are the focus of medical research, sport policy and media awareness, not enough focus, if any, has been devoted to the consideration of the jaw joint and the possibility of fracturing these basal skull temporal bones associated with the forces of concussion. These basal skull fractures and pathologies are the structural injury components of concussions. The long-term consequences of concussions, jaw joint and basal skull fracture injuries are a looming national health issue with serious legal implications. Concussions and these related injuries are ending sport careers prematurely, causing distress, mental decline, behavioral changes, and financial hardships, which affect the quality of life of athletes, military personnel and their families long after their careers are over.

The compelling collision force of the helmet-to-helmet, helmet-to-chin or helmet-to-face shield common to lacrosse and football or the dangerous collision forces of the shoulder or elbow to jaw hits in basketball or stick-into-the-face in lacrosse and hockey and the damaging pugil stick to faceguard or chin or the wooden bayonet to chin in military combative training are seriously fracturing the fragile temporal bones at the base of the skull in the area of the jaw joint while causing the brain concussions. Whether intentional or unintentional, the severe impacts of these collision forces occur frequently during games, military operations and often during practice.

The helmet design for the head impacts of lacrosse, football, the military and the like, for the most part adequately protects the skull with the exception of the jaw joint complex. The 4-point chinstrap retention system when properly snapped in place, harmfully compresses the mandibular condyle of the lower jaw against the temporal bones at the base of the skull. This positioning preempts the jaw joint to more easily transmit these severe impact forces of the lower jaw impact concussions to base of the brain with greater intensity. This irritating and uncomfortable jaw joint constraint makes it difficult to maintain the chinstrap in place for extended periods of time in sports or military operations. Simply positioning or snapping the chinstraps in place can induce headaches, facial pain, discomfort and fatigue frequently experienced by many players and military personnel.

SUMMARY OF THE INVENTION

As the remedies and treatment options for concussions and their consequences are researched, it is essential that a better understanding of the anatomy and function of the jaw joint structures are studied in order to better appreciate the seriousness and consequence of these powerful lower jaw impacts as they relate to a primary mechanism of brain injury in sports and military operations. Closer attention must also be paid and studied to the site of the impact that is responsible for the lower jaw impact concussions.

The mere presence of a jaw joint has never been considered as an intimate component of the head. The recently diagnosed fractures in the jaw joint or temporal mandibular joint associated with brain concussions, have never been previously identified or considered in treatment regimens and preventative measures. However, these undiagnosed fractures have become a constant irritation to the brain and will attribute to the exacerbation and remission events of non-specific origins that frequently occur during the treatment of concussions and result in long term problems.

Organized sports personnel, concussion medical researchers, and the legal profession have no appreciation for the relationship between the jaw joint structure and brain concussions. However, some of the responsibility for the pain and suffering of brain concussions must be accepted by the society as a whole because the society has subsidized, through tax dollars, and accepted inadequate head concussion research performed with head forms that do not possess or consider the jaw joints (TMJ) in the Anthropomorphic Test Device (ATD) Impact Headform. This research approach is analogous to studying leg impacts without a knee or hip joint.

The internal surface of the skull (see FIG. 1) contains four inter-cranial compartments called cranial fossae, an anterior fossa (ACF) #1, a posterior fossa (PCF) #2 and two middle cranial fossae (MCF) #3. These fossae house and support different compartments or lobes of the brain. The ACF supports the lower portion of the frontal lobe of the brain; the PCF supports the cerebellum and hindbrain while the middle cranial fossae (the fossae relative to this invention) houses and supports the right and left temporal lobes respectively. If a person were to place his/her fingers directly in front of his/her ears while opening and closing the mouth, the person will feel and better appreciate the movement of the mandibular condyles of the lower jaw. These mandibular condyles articulate with or function against the floors of the thin and fragile middle cranial fossae temporal bones that support the temporal lobes, bilaterally.

For the first time ever, by repurposing the new and powerful 3D Cone Beam Volumetric Tomography to produce a three dimensional diagnostic and finely detailed lateral sagittal images of the jaw joint structure, the anterior cranial fossa (ACF) #1, posterior cranial fossa (PCF) #2 and middle cranial fossae (MCF) #3 and the temporal bones, this lateral sagittal scan producing the "Williams' View" (see FIG. 2) reveals the alarming anatomical relationship between the mandibular condyle #4 of the lower jaw and the floor #5 of the middle cranial fossa #3 which supports and houses the temporal lobe of the brain. This Williams view enhances the diagnostic clarity of the structural fractures and other related pathologies of the jaw joint complex. This technology also brings into focus the relationship between the adjacent ear canal #7, the thinnest and most delicate bone #5 that supports and protects the inferior surface of the brain (the floor of the middle cranial fossa), the glenoid fossa temporal bone #6 is the ceiling of the jaw joint structure which is also the floor of the MCF #5 and the mandibular condyle #4 of the lower jaw. The lower jaw impact force that causes this method of concussion causes the condyle to impact against the thin glenoid fossa directly traumatizing the temporal lobe and fracturing these thin temporal bones of the fossa and ear canal.

These temporal bone fractures constantly irritates the temporal lobes causing the post-concussion cognitive syndromes (PCS), which are defined primarily by clusters of cognitive symptoms of the temporal lobe problems. The Post-Concussion Cognitive symptoms include but are not limited to the following harmful conditions and sensations: headaches, sleep disturbances, clicking, popping and grinding sounds, pain upon open and closing the mouth, irritability, depression, mood swings, memory loss, mental confusion, ringing in the ears, behavioral changes, personality variations, slow reaction time, feeling in a fog, loss in concentration, facial and joint pains, intellectual difficulties, impaired sense of balance, teeth clenching and grinding episodes, physical loss of strength, migraine-like headaches, impaired lower jaw movements, pain with opening and closing the mouth, severe headaches and dizziness, post-traumatic stress disorders, extreme sensitivity to light and noise, being more impulsive or hostile than usual, reoccurring pulsating pains behind the eye, grinding, clicking and popping sounds when opening or closing the mouth.

The dynamic and essential functions of the mandible or lower jaw cause the condyle to constantly articulate against the fractured temporal bones; the probability is great that this constant irritation of the fractured temporal bone may enhance the development of brain encephalopathy, degenerative brain disease, post-traumatic stress disorders, and the like.

These undiagnosed jaw joint fractures will also exponentially increase the risk of future concussions with less impact force.

The same kinds of jaw joint fractures are commonly found in auto and other vehicular accident victims. At the moment of impact, the body accelerates forward leading with the head. The common injury mechanisms are (see drawing FIG. 3 & FIG. 4): The air-bag is discharged #8 at the moment of the crash. The deployment of the air-bag impact (at approximately 200 MPH) impacts the face, which drives head of the condyle onto the base of the skull like a punch to the face. This punch-like event knocks the head back, slamming it against the headrest #9. When the head impacts against the headrest, the lower jaw is slammed against the base of the skull. Both of these events produce more than enough force to fracture the thin bones in the jaw joint while concussing the brain.

All of this brain concussion information is lost because the automotive industry's military's and sports' Anthropomorphic Testing Device (ATD)-(the headform of the impact test dummies), lack the jaw joint structures, the most vital joint structure of the body. Unfortunately, jaw joint injuries relating to head trauma of any kind have not been a priority of the medical, sport, or military communities. Millions of vehicular accident victims are suffering from undiagnosed jaw joint fractures that cause the acute and chronic or long-term and debilitating post-concussion syndromes.

Military operations produce a target rich environment of jaw joint pathologies. Many of the recruits undergoing the intake process for the military will present with undiagnosed jaw joint pathologies. As a result of hand-to-hand or pugil-stick to pugil-stick combative training and other head impact encounters during the rigorous training, many military personnel will incur jaw joint injuries and suffer from the cognitive symptoms of concussions related to these fracture. The most prevalent symptom is the "exploding headache symptom".

These cognitive symptoms may further be attributed to:

(1) Kevlar helmet retention design, which constrains the jaw joint however, loose chinstraps compromise the effectiveness, safety and design of the helmet, the Helmet Position Index (HPI), and the safety of the soldier. The proper wearing of the heavy Kevlar helmet with the chinstrap apparatus secure and in place constrains and compresses the mandibular condyle into the fossa of the temporal bone of the jaw joint, which heightens the consequence of head impact injuries and concussions. This helmet retention device constraint will intensify jaw joint injuries caused by the direct effect of the overpressure that occurs as the blast wave of an explosion encounters the solider and when these forces knocks the solider down. Both of these impact events will transfer sever impact forces directly to both jaw joint sites and temporal lobes simultaneously, concussing the temporal lobes while producing multiple undiagnosed fractures in the jaw joint structures.

(2) Consider the consequences of the concussive wave of the impact force against the jaw joint produced by field artillery units with the multiple firings of 155 mm or 205 mm rounds and the like or the unilateral damage to the jaw joint caused by the repetitive firing impacts and the weapon recoils of sniper training. These events wreak havoc on the unprotected jaw joint causing concussive symptoms of headaches, facial and ear pain and the like. Protecting and stabilizing the jaw joint complex of the military personnel reduce the risk of jaw joint fractures, temporal lobe concussive events and the onset of many cognitive symptoms of concussions.

Wearing the Low Profile Articulation Jaw Joint Stabilizer (LPAJJS) device as a component of the Kevlar headgear protection device, enhances the HPI and the long term comfort of wearing the heavy Kevlar helmet with the chin strap retention system properly positioned without producing the headaches, facial pains, irritations, and fatigue now experienced by many soldiers. This ability to extend the wearing period of the properly positioned and retained Kevlar system increases the safety of the soldier, while enhancing the soldier's strength, performance, and proficiency. LPAJJS device, therefore, introduces and expands a new safety net to headgear that can help reduce the mortality rate of the soldiers. The soldier is the military's most valuable asset and his protection is a national responsibility.

Early Diagnosis and treatment of jaw joint fractures can reduce sick time/down time, and places the soldier back into military operations sooner and will have a positive economic impact on the care and ongoing rehabilitation of the brain injured individual.

(3) In fixed wing aviation, the "G" forces exert injurious stress against the jaw joint structure. Pulling G's cause compression, clenching, straining, pain, and fatigue of the jaw joint structure, which will produce headaches, impair aviation functions, and render the pilot to the state of unconsciousness.

G forces are a routine part of aerial combat. This understates the unnatural and physically punishing effects of forces 6.5 times that of gravity. To be able to withstand the G's while predicting the opponent's tactics and executing your own tactics is the acid test of the fighter pilot. At this level of entry, jaw joint pathology is inevitable with various cognitive symptoms of headaches, facial pains, balance, and the like.

Many pilots traveling in a straight plane of direction may tolerate Mach 1.5 acceleration, but maneuverability and the forces of inertia at these speeds become the major issues. Stabilizing and locking the lower jaw away from the thin temporal bones will decrease the physical variables of G-forces on the temporal bone and brain which should enhance human potential, performance, and maneuverability with greater acceleration, hence increasing the lethal performance of aerial combat in machines such as the F/A-22 RAPTOR and other fixed wing aerial fighters. By safeguarding the jaw joint from the physically punishing G forces of aviation may enable the aviator to perform physical maneuvers at greater acceleration than currently possible while decreasing the headaches and facial pains associated with the acceleration of fixed wing aviation.

(4) Rotary wing aviation personnel are being plagued by "noise induced hearing loss". The Army has developed the unique multiple access ride simulator, which is capable of duplicating the ride of any aircraft or ground vehicle in the army's inventory. This research tool is used to access the health risk and performance decrements associated with repeated impacts and vibrations produced by army ground and air vehicles.

Consider the physical effects of the following: the lower jaw or mandible is not attached to the skull and the continuous vibrational forces as demonstrated by the multiple access ride simulator will certainly cause the condyle of the lower jaw to tap against the temporal bones of the skull and ear canal. The constant and repetitive temporal bone tapping of the condyle against the ear canal will cause structural bony changes of the ear canal that will directly affect hearing. Preventing the temporal tap mechanism caused by the continuous vibrational and impact forces produced by army air ground and air vehicles will diminish the onset of noise induced hearing loss.

All exercise, strength training as well as other physical activities and stress, involves some degree of the involuntary teeth clenching mechanism. Teeth clenching associated with exercise activates an involuntary nerve reflex mechanism that is facilitated by the vague nerve. This reflex mechanism produces a sensory and motor nerve impulse response that incorporates and produces a sensory and motor nerve impulse response that incorporates physical strength and endurance and also prepares a participant for the fight or flight syndrome. Upon clenching, the sensory nerve impulse travels to the brain and stimulates the reflex mechanism activating the motor nerve impulse response. The motor nerve component of this vagal nerve reflex activates many muscle groups producing strength and endurance.

Jaw joint injuries impair the sensory nerve response of the reflex mechanism. This in turn, simplistically stated, limits the motor impulses of the reflex mechanism and the net effect is a decrease in the output of strength and endurance of the participants without their knowledge.

The Low Profile Articulation Jaw Joint Stabilizer device repositions the condyle #4 away from the preciously injured or weakened temporal bones #s 5 & 6 of the jaw joint complex while locking the teeth into upper and lower bite channels respectively which restores and enhances the clenching reflex mechanism and vagus nerve functions (see FIGS. 5 & 6). The net effect herein is the enhanced strength, performance and endurance of the wearer while enhancing speech communication, protecting this vital joint and reducing the risk of lower jaw impact concussions and jaw joint fractures. This utilization of this LPAJJS device is not important only to participants of sports and military operations but also to patients in rehabilitation, physical therapy, condition training, weight lifting, concussion therapy, and the like.

The physical forces of the clenching mechanism causing compression of the condyle against the temporal bones will also produce the exercise induced headache and other temporal mandibular joint dysfunctions experienced by many exercising participants. 10.8 million people in the U.S. suffer from TMJ problems. Accompanying the exercised induced headache is the loss of strength and endurance unbeknownst to the participant. Wearing the LPAJJS device eliminates joint stress, exercise induced headaches while increasing strength, endurance, and the physical outcome of the exercise activity. The device by physically repositioning and holding he the lower jaw in the downwardly and forwardly position increases the glottis airway space (see FIGS. 7 & 8) #10 which will prevent snoring in many individuals. It, also, enables mouth breathing through the anterior airway space #11 while clenching the teeth, maintaining better electrolyte and oxygen balance during the rigorous activities of sports and military training. The involuntary clenching occurring during exercise will also produce damaging and sheering forces that fractures the teeth in many high-end training and exercise activities, such as, weight lifting, and the like. The LPAJJS device will also dissipate these aberrant forces against the teeth, preventing tooth destruction and costly dental repairs.

U.S. Pat. Nos. 4,810,193 and 5,636,379 disclose jaw joint protective devices that provide protection for the teeth, lips, jaw, and other delicate structures of the vital cranial triad (VCT) from injury and/or for supporting the condyle of the temporomandibular joint in a relatively stable position. The VCT constitutes the condyle of the mandible, inferior lateral surface at the floor of the middle cranial fossa, and the anterior temporal tympanic bone of the ear canal.

The present invention is directed to a low profile jaw-joint therapeutic and protective device for protecting a wearer's lips, tongue, teeth, the vital cranial triad (VCT), and other oral structures within the full maxillary and mandibular arches of the mouth, and repositioning the jaw joint structure while enhancing clear speech, articulation, and sound production by eliminating the labial flanges from under the mandibular and maxillary lips, that would interfere with the lip movements and the production of enhanced articulated audible sounds. The device also locks the mandibular condyle down and forward or away from the glenoid fossa, ear canal, and the floor of the temporal lobe, while increasing the glottis airway space which reduces snoring and enhances air-flow. This device is composed of:

a) a U-shaped base (see FIG. 9) having a bilateral posterior impression chamber #12 and a low profile anterior impression chamber #13. The integrated anterior maxillary and mandibular dental arches creates the opening for the anterior airway space #11 (see FIGS. 10 & 11) and a reinforced anterior low profile dental region (see FIG. 10) that covers the incisal edge up to the incisal third of the anterior maxillary #14 and mandibular #15 arches, with an integrated maxillary #16 and mandibular #17 posterior components (see FIG. 11) having posterior buccal flanges, the maxillary #18 and mandibular #19 that are generally positioned under the buccal folds, whereby the flange areas are eliminated in the anterior region of the mandibular and maxillary arches, and the incisal edges of the maxillary component have been strengthened, supported and protected by the articulating rim #20. The mandibular lingual component has been strengthened, locked and reinforced by the mandibular lingual lock #21, where the components are adapted for securement within the maxillary and mandibular arches of the mouth, whereby the mandibular lingual lock component offsets the lower jaw downwardly and forwardly from the maxillary component that enhances the anterior airway space #11 and the mandible is set in a protruding-like position and the lingual lock prevents the condyle from slipping, slamming, or being driven back into the glenoid fossa of the skull;

b) a full arch occlusal impact chamber in the maxillary and mandibular components of the base is created with a first and a second material where the first material is a thermoplastic material that softens when heated to a temperature greater than body temperature but less than or equal to 100° C. and rigidly stiffens when cooled so that the device can be a thermoplastic material that can be perfectly fitted in situ, and the second material used for the remainder of the device is a harder and more resilient material than the first material that is more heat resistant than the first material for dissipation and absorption of shock imposed upon the mandible, maxilla, head and facial structures;

c) the maxillary lingual component #20 projects upwardly from the base forming with the base a maxillary channel or occlusal impact chamber for seating and protecting the maxillary teeth, creating the articulating rim or the lingual wall of the maxillary anterior dental region of the device to support the maxillary anterior teeth, and permitting the tongue of the wearer to be placed against the lingual surface of the anterior maxillary teeth to better enable articulating speech;

d) the low profile maxillary #14 and mandibular #15 reinforced anterior components cover and support the incisal edge to the incisal third of the anterior teeth from canine to canine, thus preventing interference with the lips during speech and audible sound production enhancing verbal communications;

e) the posterior mandibular component comprising the lingual flange #21A which is the continuation of the thickened and reinforced mandibular lingual lock #21 and the buccal flange #19 projecting downwardly from the base forming with the base a mandibular channel or posterior occlusal impact chamber for seating and protecting the mandibular teeth, and the reinforced mandibular deep labial flange to support and guide the mandible such that the mandible is engineered into a functionally protected prognathic position creating a force attenuating recoil space of the jaw-joint; and f) (See FIGS. 8, 10 & 11) a functional anterior airway space #11 or passageway from canine to canine in the anterior of the integrated component to facilitate breathing, expectorating, and speaking; wherein the reinforced anterior dental regions of the maxillary and mandibular components and the posterior components bilaterally maintain the framework and shape of the device and dissipate and absorb shocks imposed upon the wearer's head.

DETAILED DESCRIPTION OF THE INVENTION

Figure 1:
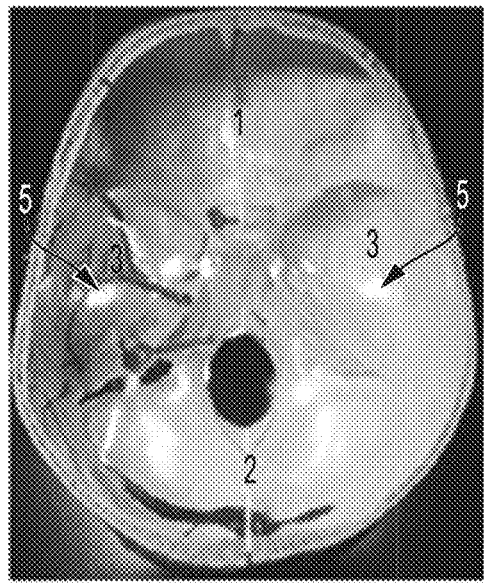
FIG. 1 is the internal cranial view of the skull.
Figure 2:
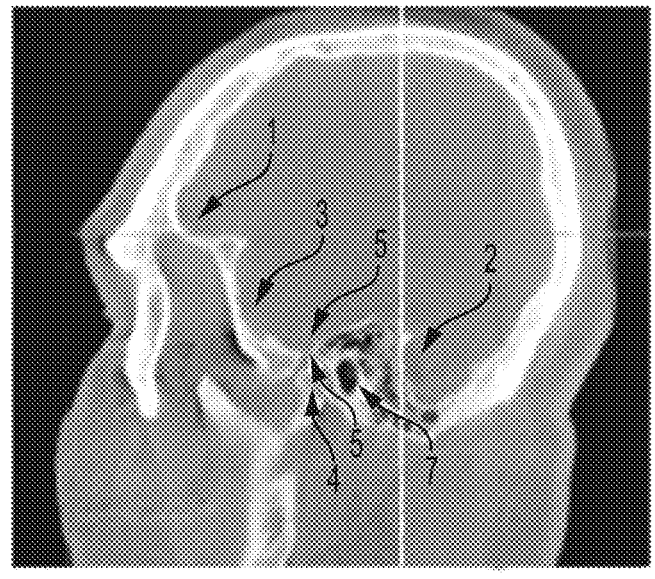
FIG. 2 is the Williams scan view of the skull illustrating the critical relationship between the condyle of the lower jaw to the middle cranial and temporal bones of the skull.
Figure 3:
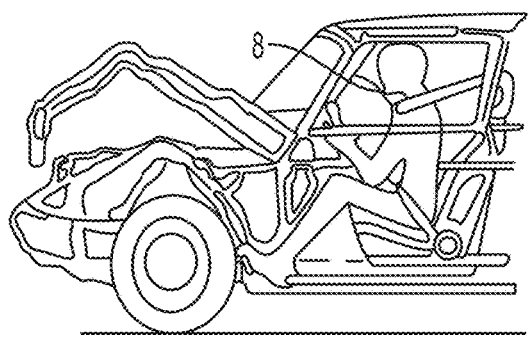
FIG. 3 is the jaw joint impact injury of an auto accident with deployment of the airbag.
Figure 4:
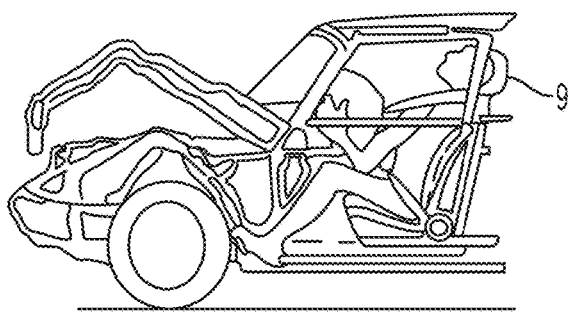
FIG. 4 is the second jaw joint impact injury of an auto accident caused by the head impacting against the head rest.

In the drawings, like numerals indicate like elements throughout. Certain terminology is used herein for convenience only and is not to be taken as a limitation on the present invention. The following describes preferred embodiments of the present invention. However, it should be understood, based on this disclosure, that the invention is not limited by the preferred embodiments described herein.

Figure 5:
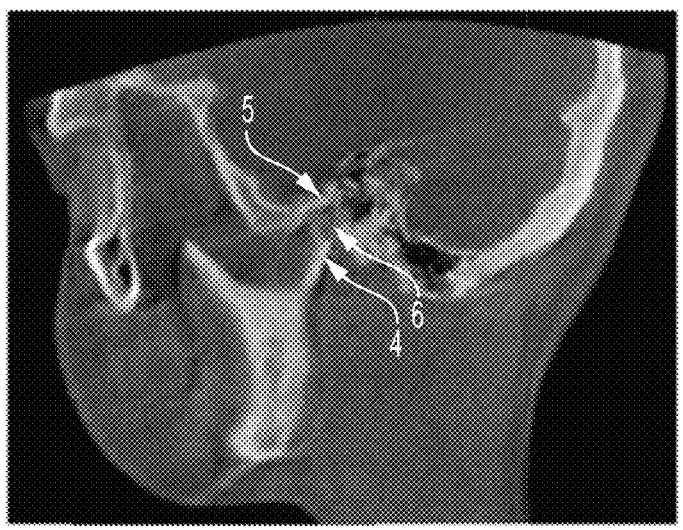
FIG. 5 is the jaw joint image of lateral sagittal scan without a mouth guard in place.
Figure 6:
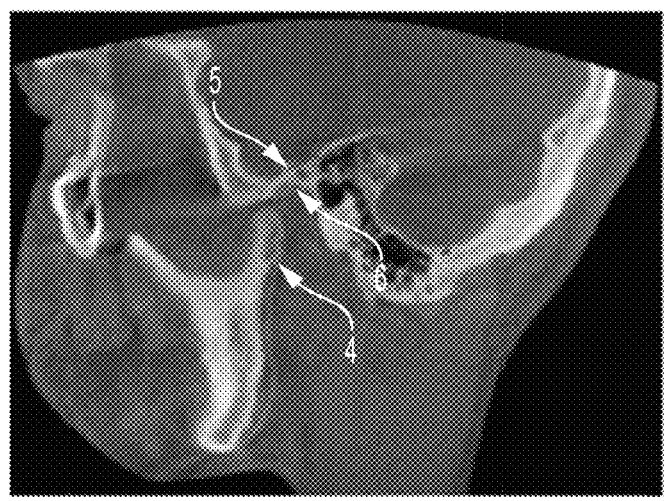
FIG. 6 is the jaw joint image of lateral sagittal scan with a mouth guard in accordance with an embodiment of the invention in place.
Figures 7, 8:
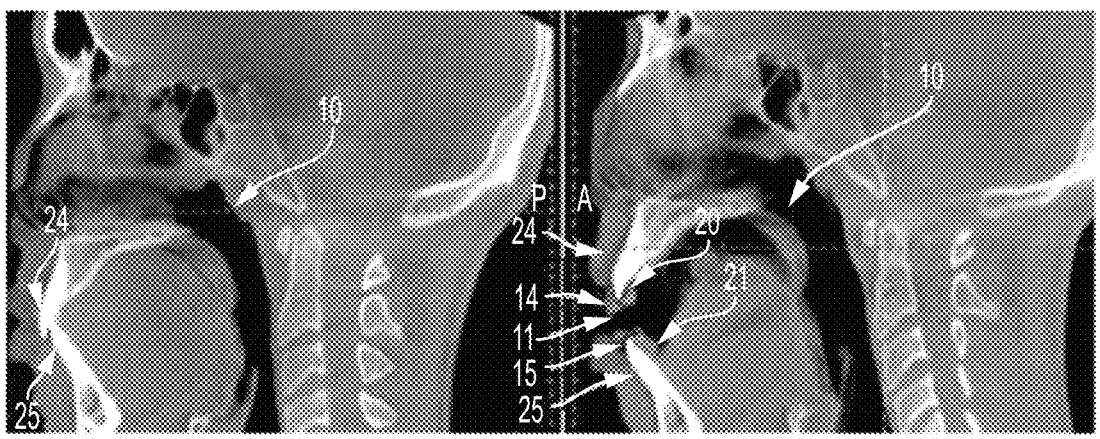
FIG. 7 is the mid-sagittal scan view without a mouth guard in place.
FIG. 8 is the mid-sagittal scan view with a mouth guard in accordance with an embodiment of the invention in place.
Figure 9:
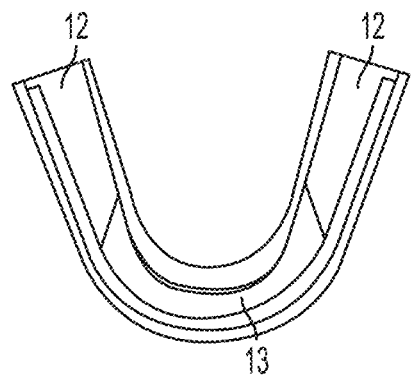
FIG. 9 is an occlusal or top view of a mouth guard in accordance with an embodiment of the invention.
Figure 10:
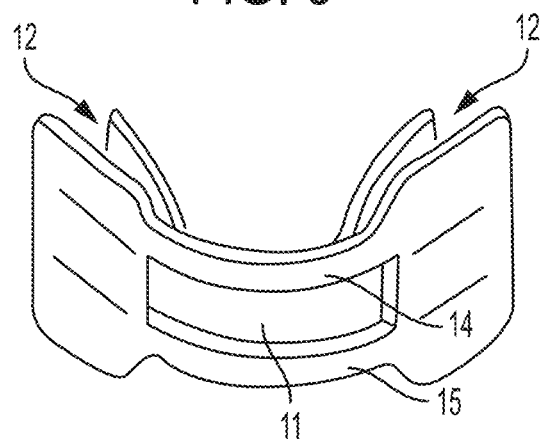
FIG. 10 is a frontal view of the low profile of a mouth guard in accordance with an embodiment of invention.
Figure 11:
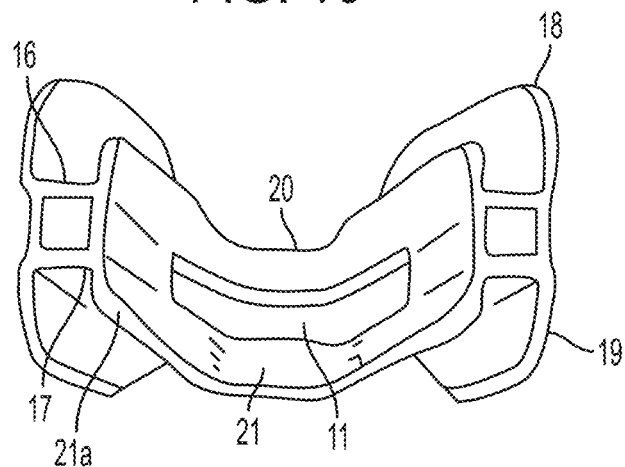
FIG. 11 is the lingual view of the low profile of a mouth guard in accordance with an embodiment of invention.
Figure 12:
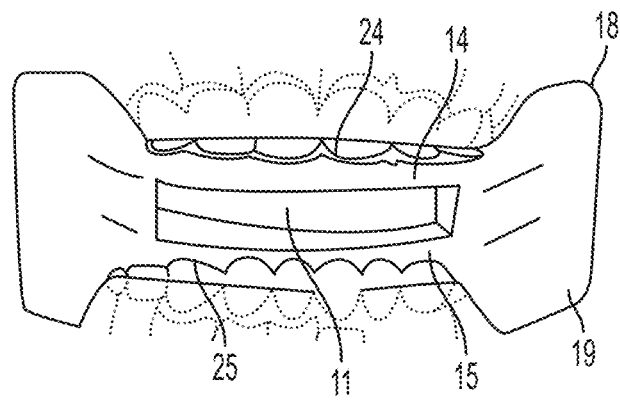
FIG. 12 is a frontal view of a mouth guard in accordance with an embodiment of the invention in place showing the device covers the incisal edge up to the cervical third of the teeth, anterior airway space and buccal flanges.
Figure 13:
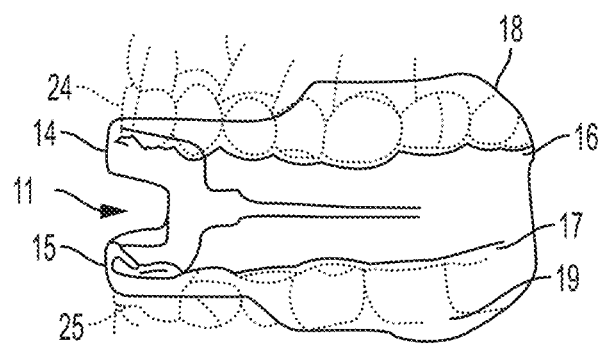
FIG. 13 is a side view of a mouth guard in accordance with an embodiment of the invention in place showing occlusal impact chambers of the upper and lower arches, anterior airway space and buccal flanges.
Figure 14:
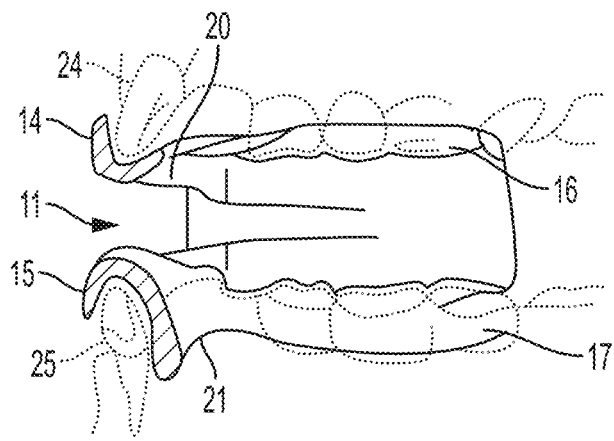
FIG. 14 is the mid-sagittal view of a mouth guard in accordance with an embodiment of the invention in place showing the occlusal impact chambers, anterior airway space and the mandibular lingual lock which secure the repositioning of mandibular arch.

It has been surprisingly found that this mouth guard device can achieve multi-tasking by not only providing protection to the oral cavity, jaw joint, and enhancing the teeth clenching reflex mechanism (TCRM) but also can enhance speech communication while wearing the device This device eliminates the mandibular and maxillary labial flanges extending under the lips and prevents impingement of the labial frenulum, however, creates the reinforced maxillary #14 and mandibular #15 anterior bite plates which secures and protects the incisal third of the maxillary #24 and mandibular #25 anterior incisal teeth (see drawings FIGS. 12, 13 & 14)). This component of the device eliminates the interference and irritation of the upper and lower lips produced when forming words, enhancing the production and clarity of sounds and articulation at variable high and low frequencies. The #14 & 15 (see FIGS. 10, 12, 13 & 14) shows the reinforced maxillary and mandibular flanges respectively covering the incisal edge up to the incisal third of the anterior teeth without the flange height being inserted under the lip, which interferes with speech; however, the posterior buccal flanges #18 &19 are present in the posterior area, which lends to the strength and stability of the device The posterior buccal flanges #18 & 19 seat between the cheeks and the teeth and may extend into the buccal fold (see FIGS. 11,12 &13). The posterior occlusal impression chamber #16 & 17 (see drawings, FIGS. 11, 13 & 14) creates the stabilizing impression of the maxillary and mandibular teeth. Clear enunciable and audible speech communication is essential for many potential wearers of protective intra-oral action devices, such as mouth guards and the like, for various collision sports and military events. This inability to clearly communicate while wearing the various intra-oral devices is vital to many activities and is the principal reasons that mouth guard devices are not and cannot be worn by many participants of high or low impact activities or military events. The LPAJJS device of the present invention reduces the risk of lower jaw impact concussions, knock-outs, and jaw joint fractures of the temporal bone by stabilizing and locking the lower jaw into the LPAJJS device, by way of the reinforced maxillary and mandibular anterior bite plates #14 & 15 which become the anterior occlusal impression chambers and the posterior occlusal impression chamber #16 & 17 together forming the bite registration and the mandibular lingual lock #21 (see drawing, FIGS. 9 through 14)), creating the significant safety space between the condyle #4 of the lower jaw and temporal bones #5 & 6 of the skull (see FIGS. 5 & 6). This is achieved by the upper and lower teeth being locked, into the anterior occlusal impression chamber #14 & 15 and into the posterior occlusal impression chambers #16 & 17 and the opening of the anterior airway space #11 working in concert with the mandibular lingual lock #21, which locks and holds the mandible in the stable position to prevents the distal movement and slamming of the condyles against the base of the temporal bones of the skull with the head and jaw impact of sports and combative military training. The created safety space between the condyle #4 and the glenoid temporal bone #6 (see FIGS. 5 & 6,) of the LPAJJS device also prevents the condyle from compressing against the temporal bones with the proper wearing of headgear and the four-point chinstrap retention system in place.

The headgear and chinstrap retention apparatus designs do not take into consideration the presence of the jaw joint structure or the protection of this vital joint. The chinstrap retention of the headgear creates the safety net for the headgear by preventing the roll-off mechanism and establishing the compliance of the Helmet Position Index (HPI). However, this proper chinstrap retention positioning of the headgear irritates, constrains, and injures the jaw joint structures by compressing the lower jaw onto the base of the skull. This positioning increases the injury potential for the temporal lobe of the brain and the jaw joint fractures while adding to the difficulty to the properly wearing of the headgear with the chin-strap in place for lengthy periods of time. Snapping the chin-straps to secure the helmet in place will produce irritation, fatigue, and headaches with many athletes and soldiers. The invention, by repositioning the lower jaw, takes the temporal bone out of harm's way, increasing strength, wear time, and the physical proficiency of the wearer.

Wearing the LPAJJS device as a component of Kevlar headgear protective device will enhance the HPI and the long term comfort of wearing the heavy Kevlar helmet with the chin strap retention system properly positioned without producing headaches, facial pain, irritations, and fatigue now experienced by many soldiers. This invention extends the wearing period of the properly positioned and retained Kevlar system increases the safety and welfare of the soldier, while enhancing his strength, performance, and proficiency. The LPAJJS device, therefore, introduces and expands a new safety net to headgear that can help reduce the mortality rate of soldiers. The soldier is the military's most valuable asset and the soldier's protection is a national responsibility.

Early diagnosis and treatment of jaw joint fractures can reduce sick time/down time and place the soldier back into military operations sooner and will have a positive economic impact on the care and ongoing rehabilitation of the brain injured individual.

In fixed wing aviation, the "G" forces exert injurious stress against the jaw joint structure. Pulling G's-causes compression, clenching, straining, pain, and fatigue of the jaw joint structure, which will produce headaches, impair aviation functions, and lend the pilot to the state of unconsciousness. G forces are the routine part of aerial combat. This understates the unnatural and physically punishing effects of forces 6.5 times that of gravity. To be able to withstand the G's while predicting the opponent's tactics and executing your own is the acid test of the fighter pilot. At this level of entry, jaw joint pathology is inevitable with various cognitive symptoms of headaches, facial pains, balance and the like.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. A jaw-joint therapeutic and protective device for protecting a wearer's lips, tongue, teeth, and vital cranial triad (VCT), comprising:

a U-shaped base comprising:
  a maxillary component having a maxillary impression chamber configured to extend from a first maxillary molar to an opposite second maxillary molar of an end user,
  a mandibular component having a mandibular impression chamber configured to extend from a first mandibular molar to an opposite second mandibular molar of the end user;
  a bilateral posterior dental region comprising mandibular arches and maxillary arches configured to form an opening for an anterior airway space;
  a low profile reinforced anterior dental region configured to cover only an incisal edge up to a cervical third of maxillary anterior teeth and mandibular anterior teeth of an end user;
  a functional air passageway formed in the low profile reinforced anterior dental region that is configured to extend from canine to canine of the end user to facilitate breathing, expectorating, and speaking;
  an occlusal impact chamber comprising a first material and a second material, the first material being a thermoplastic material that softens at temperatures greater than body temperature and rigidly stiffens when cooled, the second material being a more resilient material than the first material and being more heat resistant than the first material;
the maxillary component including:
  a maxillary lingual wall and maxillary buccal wall for seating and protecting maxillary teeth, the maxillary lingual wall including an articulating rim configured to facilitate placement of a tongue of the end user for articulating speech;
  a maxillary posterior flange area configured to be positioned under maxillary buccal folds of the end user;
the mandibular component including:
  a mandibular lingual wall and mandibular buccal wall for seating and protecting mandibular teeth and a reinforced mandibular labial flange configured to position a mandible of the end user in a functionally protected prognathic position thereby creating a force attenuating recoil space;
  a mandibular posterior flange area configured to be positioned under the mandibular buccal folds of the end user,
wherein the mandibular component is offset downwardly and forwardly from the maxillary component thereby positioning a mandibular condyle of the end user down and forward from a glenoid fossa, ear canal, and floor of a temporal lobe of the end user and increasing a glottis airway space of the end user, and
wherein, in a frontal view, a first height of the maxillary buccal walls is greater than a second height of a maxillary portion of the low profile reinforced anterior dental region, and a third height of the mandibular buccal walls is greater than a fourth height of a mandibular portion of the low profile reinforced anterior dental region.

2. The device of claim 1, wherein the device does not include a maxillary anterior labial flange in the anterior region between the maxillary canine teeth.

3. The device of claim 2, wherein the device does not include a mandibular anterior labial flange in the anterior region between the mandibular canine teeth.

4. The device of claim 1, wherein the device does not include a mandibular anterior labial flange in the anterior region between the mandibular canine teeth.

5. The device of claim 1, wherein the anterior airway space of the device facilitates breathing and speech.

6. The device of claim 1, wherein the device is configured to reduce lower jaw impact concussions and fractures attributable to the temporal bones associated with the condyle of the lower jaw and impact of the temporal bones at the base of the skull.

7. The device of claim 1, wherein the device is configured to reduce impact to the condyle of the lower jaw and suppress the mandibular condyle from being driven onto the temporal bone and the ear canal.

8. The device of claim 1, wherein the device is configured to suppress condyle tapping the temporal bones of the skull and ear canal.

9. The device of claim 1, wherein the device is configured to transfer compressive forces from the jaw joint space to the teeth.

10. The device of claim 1, wherein the device is configured to enhance oxygen intake while an end user clenches their teeth against the device in a clenched position due to the anterior airway space and the low profile reinforced anterior dental region only covering the incisal edge up to the cervical third of the maxillary and mandibular anterior teeth of the end user.

11. The device of claim 1, wherein the device is configured to reduce fractures of the anterior wall of the ear canal.

12. The device of claim 1, wherein the device is configured to reposition the mandible of the end user down and forward relative to a natural position of the mandible of the end user.

13. The device of claim 1, wherein the device, is configured to urge the mandibular arches and maxillary arches of the end user into alignment such that impact forces may be transferred between the mandibular arches and maxillary arches.

14. A low profile mouthguard, comprising:
  a substantially U-shaped base comprising a maxillary component, a mandibular component, and an anterior airway aperture,
  the maxillary component comprising a maxillary impression chamber configured to extend from a first maxillary molar to an opposite second maxillary molar of an end user and being defined by a maxillary anterior flange and a maxillary posterior flange;
  the maxillary anterior flange including a first maxillary buccal wall, a second maxillary buccal wall opposite the first maxillary buccal wall, and a low-profile maxillary anterior dental wall between the first maxillary buccal wall and the second maxillary buccal wall, the low-profile maxillary anterior dental wall being configured to cover at least an incisal edge up to a cervical third of maxillary anterior teeth of the end user,
  wherein, in a frontal view, a height of the first maxillary buccal wall and a height of the second maxillary buccal wall are each greater than a height of the low-profile maxillary anterior dental wall;
  the maxillary posterior flange including a maxillary lingual wall, and having an average height that is less than an average height of the maxillary anterior flange;
  the mandibular component comprising a mandibular impression chamber configured to extend from a first mandibular molar to an opposite second mandibular molar of the end user and being defined by a mandibular anterior flange and a mandibular posterior flange;

the mandibular anterior flange including: a first mandibular buccal wall, a second mandibular buccal wall opposite the first mandibular buccal wall, and a low-profile mandibular anterior dental wall between the first mandibular buccal wall and the second mandibular buccal wall, the low-profile mandibular anterior dental wall being configured to cover at least an incisal edge up to a cervical third of mandibular anterior teeth of the end user;

wherein, in a frontal view, a height of the first mandibular buccal wall and a height of the second mandibular buccal wall are each greater than a height of the low-profile mandibular anterior dental wall;

the mandibular posterior flange including a mandibular lingual wall, and having an average height that is less than an average height of the mandibular anterior flange;

wherein the anterior airway aperture extends through the U-shaped base between the maxillary component and the mandibular component.

15. The mouthguard of claim 14, wherein the mandibular component is offset downwardly and forwardly from the maxillary component thereby positioning a mandibular condyle of the end user down and forward from a glenoid fossa, ear canal, and floor of a temporal lobe of the end user and increasing a glottis airway space of the end user.

16. The mouthguard of claim 14, wherein the low-profile maxillary anterior dental wall is configured to cover only an incisal edge up to a cervical third of maxillary anterior teeth of the end user, and the low-profile mandibular anterior dental wall is configured to cover only an incisal edge up to a cervical third of mandibular anterior teeth of the end user.

* * * * *